United States Patent
Greene et al.

(10) Patent No.: US 10,660,542 B2
(45) Date of Patent: *May 26, 2020

(54) RFID MARKERS AND SYSTEMS AND METHODS FOR IDENTIFYING AND LOCATING THEM

(71) Applicant: CIANNA MEDICAL, INC., Aliso Viejo, CA (US)

(72) Inventors: John E. Greene, Valley Center, CA (US); Nikolai F. Rulkov, San Diego, CA (US)

(73) Assignee: Cianna Medical, Inc., Aliso Viejo, CA (US)

(*) Notice: Subject to any disclaimer, the term of this patent is extended or adjusted under 35 U.S.C. 154(b) by 22 days.

This patent is subject to a terminal disclaimer.

(21) Appl. No.: 15/993,559

(22) Filed: May 30, 2018

(65) Prior Publication Data
US 2018/0271401 A1  Sep. 27, 2018

Related U.S. Application Data

(63) Continuation-in-part of application No. 15/658,275, filed on Jul. 24, 2017, now Pat. No. 10,383,544, (Continued)

(51) Int. Cl.
*A61B 5/06* (2006.01)
*A61B 90/30* (2016.01)
(Continued)

(52) U.S. Cl.
CPC ............ *A61B 5/064* (2013.01); *A61B 5/0507* (2013.01); *A61B 5/4312* (2013.01);
(Continued)

(58) Field of Classification Search
CPC ................... A61B 5/064; A61B 90/39; A61B 2090/3904–3995
See application file for complete search history.

(56) References Cited

U.S. PATENT DOCUMENTS 5,190,059 A * 3/1993 Fabian .................... A61B 5/06
128/899
5,361,070 A  11/1994 McEwan
(Continued)

FOREIGN PATENT DOCUMENTS

EP  1374793 A1  2/2004
EP  1510183 A1  3/2005
(Continued)

OTHER PUBLICATIONS

Agents from the European Patent Office; International Search Report and Written Opinion from corresponding International Application No. PCT/US2018/035219, dated Sep. 20, 2018, 12 pages.
(Continued)

*Primary Examiner* — Thaddeus B Cox
(74) *Attorney, Agent, or Firm* — Stoel Rives LLP (57) ABSTRACT

Systems and methods are provided for identifying or locating a tag within a patient's body that include a probe that transmits synchronized electromagnetic signals, e.g., RF energy, and optical signals, e.g., infrared light pulses into the patient's body, whereupon the tag converts the optical signals into electrical energy to open and close a switch in the tag to modulate signals, e.g., backscatter signals, transmitted by the tag in response to the electromagnetic signals. For example, the tag may include photodiodes coupled to the switch that transforms the optical signals to alternately short the antenna to modulate the backscatter signals. Alternatively, the tag may include a smart circuit that harvests electrical energy from the optical signals to power the smart circuit and/or modulate the backscatter signals, e.g., to include data related to the tag and/or alternate the tag between an information mode and a distance mode.

20 Claims, 6 Drawing Sheets

Related U.S. Application Data which is a continuation of application No. 14/165,253, filed on Jan. 27, 2014, now Pat. No. 9,713,437, application No. 15/993,559, which is a continuation-in-part of application No. 15/446,944, filed on Mar. 1, 2017.

(60) Provisional application No. 62/512,692, filed on May 30, 2017, provisional application No. 61/757,130, filed on Jan. 26, 2013, provisional application No. 61/800,046, filed on Mar. 15, 2013, provisional application No. 62/303,312, filed on Mar. 3, 2016.

(51) Int. Cl.
| | | |
|---|---|---|
| *A61B 5/05* | (2006.01) | |
| *A61B 5/00* | (2006.01) | |
| *A61B 90/00* | (2016.01) | |
| *A61B 90/98* | (2016.01) | |
| *A61B 34/20* | (2016.01) | |

(52) U.S. Cl.
CPC ............ *A61B 5/6847* (2013.01); *A61B 90/39* (2016.02); *A61B 90/98* (2016.02); *H05K 999/99* (2013.01); *A61B 2034/2048* (2016.02); *A61B 2090/306* (2016.02); *A61B 2090/309* (2016.02); *A61B 2090/397* (2016.02); *A61B 2090/3908* (2016.02); *A61B 2090/3925* (2016.02); *A61B 2090/3966* (2016.02); *A61B 2090/3975* (2016.02); *A61B 2090/3987* (2016.02); *A61B 2090/3991* (2016.02)

(56) References Cited

U.S. PATENT DOCUMENTS

| | | | |
|---|---|---|---|
| 5,573,012 | A | 11/1996 | McEwan |
| 5,764,162 | A | 6/1998 | Ehrlich |
| 5,766,208 | A | 6/1998 | McEwan |
| 5,853,366 | A | 12/1998 | Dowlatshahi |
| 5,879,357 | A | 3/1999 | Heaton et al. |
| 6,061,589 | A | 5/2000 | Bridges et al. |
| 6,144,300 | A | 11/2000 | Dames |
| 6,226,548 | B1 | 5/2001 | Foley |
| 6,233,479 | B1 | 5/2001 | Haddad et al. |
| 6,363,940 | B1 | 4/2002 | Krag |
| 6,492,933 | B1 | 12/2002 | McEwan |
| 6,496,717 | B2 | 12/2002 | Cox et al. |
| 6,575,991 | B1 | 6/2003 | Chesbrough et al. |
| 6,725,083 | B1 | 4/2004 | Burbank et al. |
| 6,914,552 | B1 | 7/2005 | McEwan |
| 7,174,201 | B2 | 2/2007 | Govari et al. |
| 7,569,065 | B2 | 8/2009 | Chesbrough et al. |
| 8,052,708 | B2 | 11/2011 | Chesbrough et al. |
| 2003/0004411 | A1 | 1/2003 | Govari et al. |
| 2003/0018246 | A1 | 1/2003 | Govari et al. |
| 2003/0036713 | A1 | 2/2003 | Bouton et al. |
| 2003/0088186 | A1 | 5/2003 | Doody |
| 2003/0192557 | A1 | 10/2003 | Krag et al. |
| 2005/0036945 | A1 | 2/2005 | Thomas et al. |
| 2005/0059884 | A1 | 3/2005 | Krag |
| 2005/0096589 | A1 | 5/2005 | Shachar |
| 2006/0025795 | A1 | 2/2006 | Chesbrough et al. |
| 2006/0258933 | A1 | 11/2006 | Ellis et al. |
| 2007/0038014 | A1 | 2/2007 | Cox et al. |
| 2007/0093726 | A1 | 4/2007 | Leopold et al. |
| 2007/0100666 | A1 | 5/2007 | Stivoric |
| 2007/0135711 | A1 | 6/2007 | Chernomorsky |
| 2007/0195929 | A1 | 8/2007 | Ruchala |
| 2007/0243225 | A1 | 10/2007 | McKay |
| 2008/0027313 | A1 | 1/2008 | Shachar |
| 2008/0071169 | A1 | 3/2008 | Craddock et al. |
| 2008/0086046 | A1 | 4/2008 | Petcavich et al. |
| 2008/0200802 | A1 | 8/2008 | Bhavaraju et al. |
| 2008/0269601 | A1 | 10/2008 | Schwamb |
| 2008/0281190 | A1 | 11/2008 | Petcavich et al. |
| 2009/0015832 | A1 | 1/2009 | Popovic et al. |
| 2009/0157068 | A1 | 6/2009 | Kallel et al. |
| 2009/0216115 | A1 | 8/2009 | Seilar |
| 2009/0248014 | A1 | 10/2009 | Shachar et al. |
| 2009/0281422 | A1 | 11/2009 | Salama et al. |
| 2009/0299174 | A1 | 12/2009 | Wright et al. |
| 2010/0234792 | A1 | 9/2010 | Dacey |
| 2010/0275934 | A1* | 11/2010 | Keren ................. G01D 5/2066 128/899 |
| 2011/0313288 | A1* | 12/2011 | Chi Sing .............. A61B 5/0507 600/437 |
| 2015/0349150 | A1 | 12/2015 | Carey et al. |
| 2016/0294056 | A1 | 10/2016 | Manteghi et al. |
| 2017/0007352 | A1 | 1/2017 | King et al. |

FOREIGN PATENT DOCUMENTS

| | | | |
|---|---|---|---|
| WO | 0239918 | A1 | 5/2002 |
| WO | 2004032779 | A1 | 4/2004 |
| WO | 2007087447 | A2 | 8/2007 |
| WO | 2007117478 | A2 | 10/2007 |

OTHER PUBLICATIONS

International Search Report and Written Opinion dated May 24, 2017 for PCT/US2017/020260.

http://www.theradarreflectorsite.org.WebManuscript;, Chapter 6: Passive Radar Reflector Elements; date not available ,64-81.

Azevedo, et al., Micropower Impluse Radar, Science & Technology Review ,Jan./Feb. 1996 ,7 pgs.

Hagness, et al., Three-Dimensional FDTD Analysis of a Pulsed Microwave Confocal System for Breast Cancer Detection, IEEE Transaction on Antennas and Propagation, vol. 47 No. 5 ,May 1999 ,9 pgs.

Hilger, et al., ultraMEDIS—Ultra-Wideband Sensing in Medicine, INTECH ,2013 ,66 pgs.

Hughes, et al., A Multi-Site Validation Trial of Radioactive Seed Localization as an Alternative to Wire Localization, The Breast Journal, vol. 14 No. 2, Blackwell Publishing Inc. ,2008 ,5 pgs.

Krishnan, et al., UWB-IR Active Reflector for High Precision Ranging and Positioning Applications, Institute of Infocomm Research, A Star Singapore, IEEE ,2010 ,14-18.

Nilavalan, et al., Wideband Microstrip Patch Antenna Design for Breast Cancer Tumor Detection, IEEE Xplore/IEEE.org, Institution of Engineering and Technology ,Apr. 30, 2007 ,1 pg.

Shannon, et al., Dialectric-Filled Slotline Bowtie Antenna for Breast Cancer Detection, Electronics Letters, 31, vol. 41 No. 7 ,Mar. 2005 ,2 pgs.

Stephan, et al., Wire Localization Procedure—Breast Biopsy of Lumpectomy, About.com/Breast Cancer, American Cancer Society/ Ohio State Medical Center ,Sep. 8, 2008 ,2 pgs.

Yun, et al., Broadband Cross-Polarized bowtie Antenna, Department of Electrical and Computer Engineering, University of Calgary, Calgary, Alberta, CA, IEEE ,2003 ,1091-1094.

Office Action dated Mar. 19, 2020 for U.S. Application No. 15/446,944.

Ahmadian, et al., Miniture Transmittter for Implantable Micro Systems, Proceedings of the 25th Annual International conference of the IEEE Embs, Cancun Mexico ,Sep. 17-21, 2003.

\* cited by examiner

FIG. 6 ns and Systems and
RFID MARKERS AND SYSTEMS AND METHODS FOR IDENTIFYING AND LOCATING THEM

RELATED APPLICATION DATA

The present application claims benefit of U.S. provisional application Ser. No. 62/512,692, filed May 30, 2017, and is a continuation-in-part of co-pending application Ser. No. 15/658,275, filed Jul. 24, 2017, which is a continuation of Ser. No. 14/165,253, filed Jan. 27, 2014, now U.S. Pat. No. 9,713,437, which claims benefit of provisional application Ser. No. 61/757,130, filed Jan. 26, 2013, and 61/800,046, filed Mar. 15, 2013. The present application is also a continuation-in-part of co-pending application Ser. No. 15/446,944, filed Mar. 1, 2017, which claims benefit of provisional application Ser. No. 62/303,312, filed Mar. 3, 2016. The entire disclosures of these applications are expressly incorporated by reference herein.

FIELD OF THE INVENTION

The present invention relates to implantable markers or tags, e.g., RFID tags, and to systems and methods for localizing such tags within a patient's body, e.g., during surgical procedures or other procedures, such as during lumpectomy procedures.

BACKGROUND

Before a biopsy or surgical procedure to remove a lesion within a breast, e.g., during a lumpectomy procedure, the location of the lesion must be identified. For example, mammography or ultrasound imaging may be used to identify and/or confirm the location of the lesion before the procedure. The resulting images may be used by a surgeon during the procedure to identify the location of the lesion and guide the surgeon, e.g., during dissection to access and/or remove the lesion. However, such images are generally two dimensional and therefore provide only limited guidance for localization of the lesion since the breast and any lesion to be removed are three-dimensional structures. Further, such images may provide only limited guidance in determining a proper margin around the lesion, i.e., defining a desired specimen volume to be removed.

To facilitate localization, immediately before a procedure, a wire may be inserted into the breast, e.g., via a needle, such that a tip of the wire is positioned at the location of the lesion. Once the wire is positioned, it may be secured in place, e.g., using a bandage or tape applied to the patient's skin where the wire emerges from the breast. With the wire placed and secured in position, the patient may proceed to surgery, e.g., to have a biopsy or lumpectomy performed.

One problem with using a wire for localization is that the wire may move between the time of placement and the surgical procedure. For example, if the wire is not secured sufficiently, the wire may move relative to the tract used to access the lesion and consequently the tip may misrepresent the location of the lesion. If this occurs, when the location is accessed and tissue removed, the lesion may not be fully removed and/or healthy tissue may be unnecessarily removed. In addition, during the procedure, the surgeon may merely estimate the location of the wire tip and lesion, e.g., based on mammograms or other images obtained during wire placement, and may proceed with dissection without any further guidance. Again, since such images are two dimensional, they may provide limited guidance to localize the lesion being treated or removed.

Alternatively, it has been suggested to place a radioactive seed to provide localization during a procedure. For example, a needle may be introduced through a breast into a lesion, and then a seed may be deployed from the needle. The needle may be withdrawn, and the position of the seed may be confirmed using mammography. During a subsequent surgical procedure, a hand-held gamma probe may be placed over the breast to identify a location overlying the seed. An incision may be made and the probe may be used to guide excision of the seed and lesion.

Because the seed is delivered through a needle that is immediately removed, there is risk that the seed may migrate within the patient's body between the time of placement and the surgical procedure. Thus, similar to using a localization wire, the seed may not accurately identify the location of the lesion, particularly, since there is no external way to stabilize the seed once placed. Further, such gamma probes may not provide desired precision in identifying the location of the seed, e.g., in three dimensions, and therefore may only provide limited guidance in localizing a lesion.

Accordingly, apparatus and methods for localization of lesions or other tissue structures in advance of and/or during surgical, diagnostic, or other medical procedures would be useful.

SUMMARY

The present invention is directed to implantable markers and tags, e.g., RFID tags, and to systems and methods for localizing such tags within a patient's body, e.g., during surgical procedures or other procedures, such as during lumpectomy procedures.

In accordance with an exemplary embodiment, a system is provided for identifying or locating a target region within a patient's body that includes a probe comprising one or more antennas for transmitting radiofrequency signals into a patient's body and receiving backscatter signals transmitted from the patient's body, and a light source for delivering optical signals into a patient's body; and a tag sized for implantation within a patient's body, the tag comprising an antenna, an energy converter configured to transform the optical signals from the light source into electrical energy, and a switch coupled to the energy converter such that the optical signals cause the tag to modulate backscatter signals transmitted by the antenna in response to the transmitted radiofrequency signals and received by the probe.

In accordance with another embodiment, a system is provided for identifying or locating a target region within a patient's body that includes a probe comprising one or more antennas for transmitting electromagnetic signals into a patient's body and receiving signals from the patient's body, and a light source for delivering optical signals into a patient's body; and a tag sized for implantation within a patient's body, the tag comprising an antenna, an energy converter configured to transform the optical signals from the light source into electrical energy, and a switch coupled to the energy converter such that the optical signals cause the tag to modulate electromagnetic signals transmitted by the antenna and received by the probe.

In accordance with still another embodiment, a tag is provided for introduction into a target tissue region within a patient's body that includes a coil antenna for transmitting backscatter signals in response to incident radiofrequency signals; a switch coupled to the antenna; and one or more photodiodes configured to convert light pulses received from a light source to generate a voltage to open and close the switch, thereby modulating the backscatter signals transmitted by the antenna back to a source of the incident radiofrequency signals.

In accordance with yet another embodiment, a tag is provided for introduction into a target tissue region within a patient's body that includes an antenna for transmitting backscatter signals in response to incident radiofrequency signals; a switch coupled to the antenna; and one or more photodiodes configured to convert light pulses received from a light source to generate a voltage to open and close the switch, thereby modulating the backscatter signals transmitted by the antenna back to a source of the incident radiofrequency signals.

In accordance with another embodiment, a method is provided for identifying or locating a tag implanted within a patient's body that includes placing a probe adjacent the patient's body oriented towards the tag; and activating the probe to transmit synchronized electromagnetic signals and optical signals into the patient's body, whereupon the tag transforms the optical signals into electrical energy to open and close a switch in the tag to modulate signals transmitted by the tag in response to the electromagnetic signals.

Other aspects and features of the present invention will become apparent from consideration of the following description taken in conjunction with the accompanying drawings.

BRIEF DESCRIPTION OF THE DRAWINGS

These and other features, aspects, and advantages of the present disclosure will become better understood with regard to the following description, appended claims, and accompanying drawings where:

DETAILED DESCRIPTION OF THE EXEMPLARY EMBODIMENTS

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Figure 1:
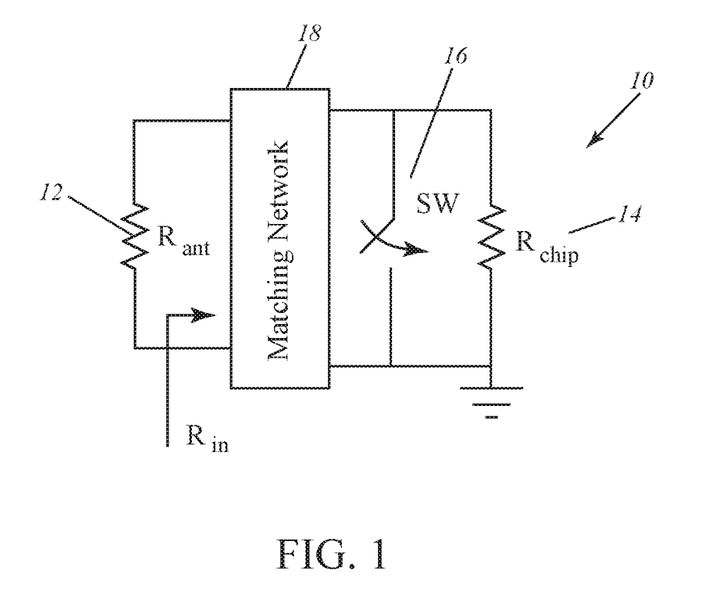
FIG. 1 shows a schematic of an exemplary embodiment of a RF energy powered RFID tag.
Figure 2:
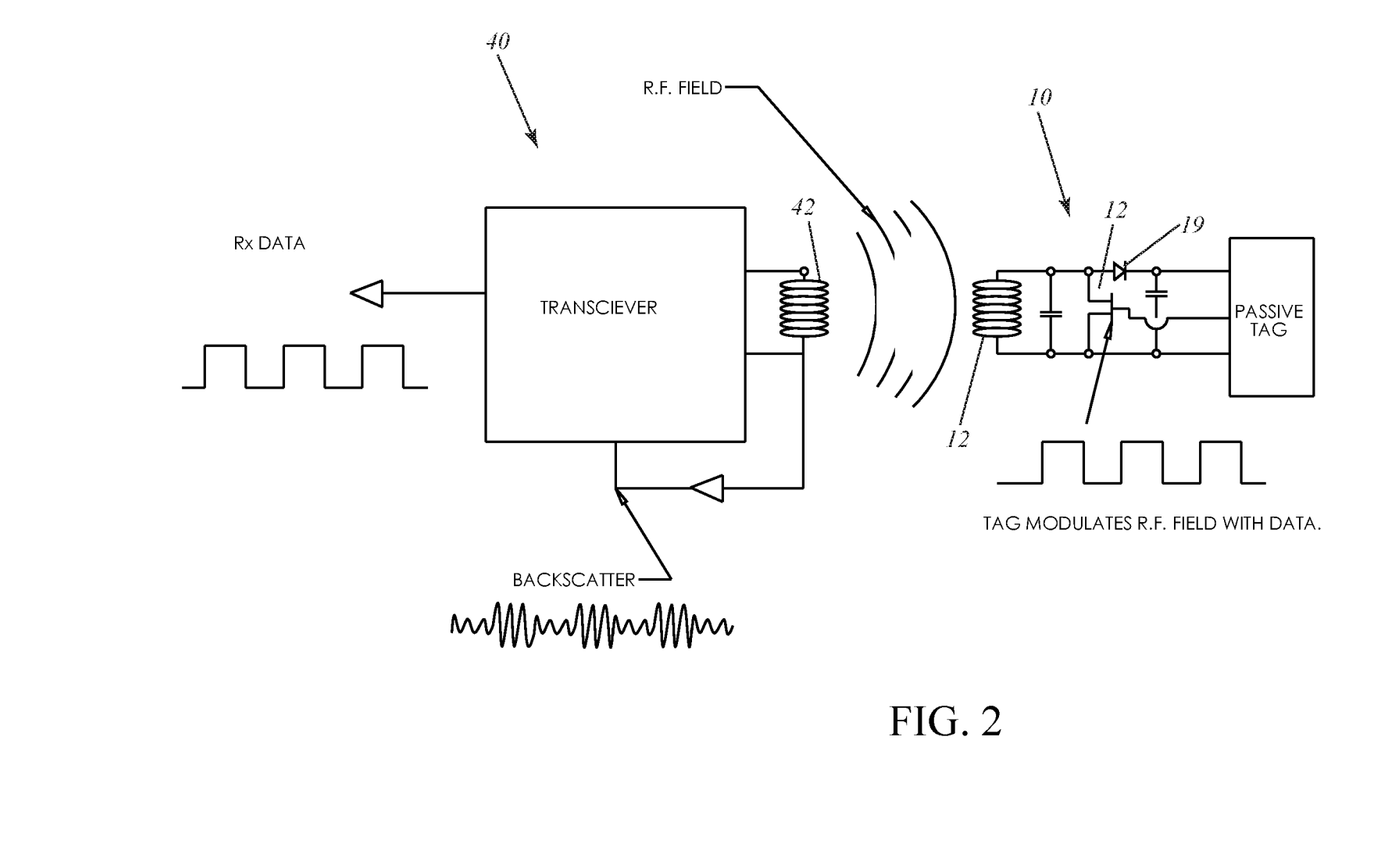
FIG. 2 is a schematic showing an exemplary system including an RFID tag implantable within a patient's body and a probe or reader transmitting RF energy and establishing communication with the tag.
Figure 3:
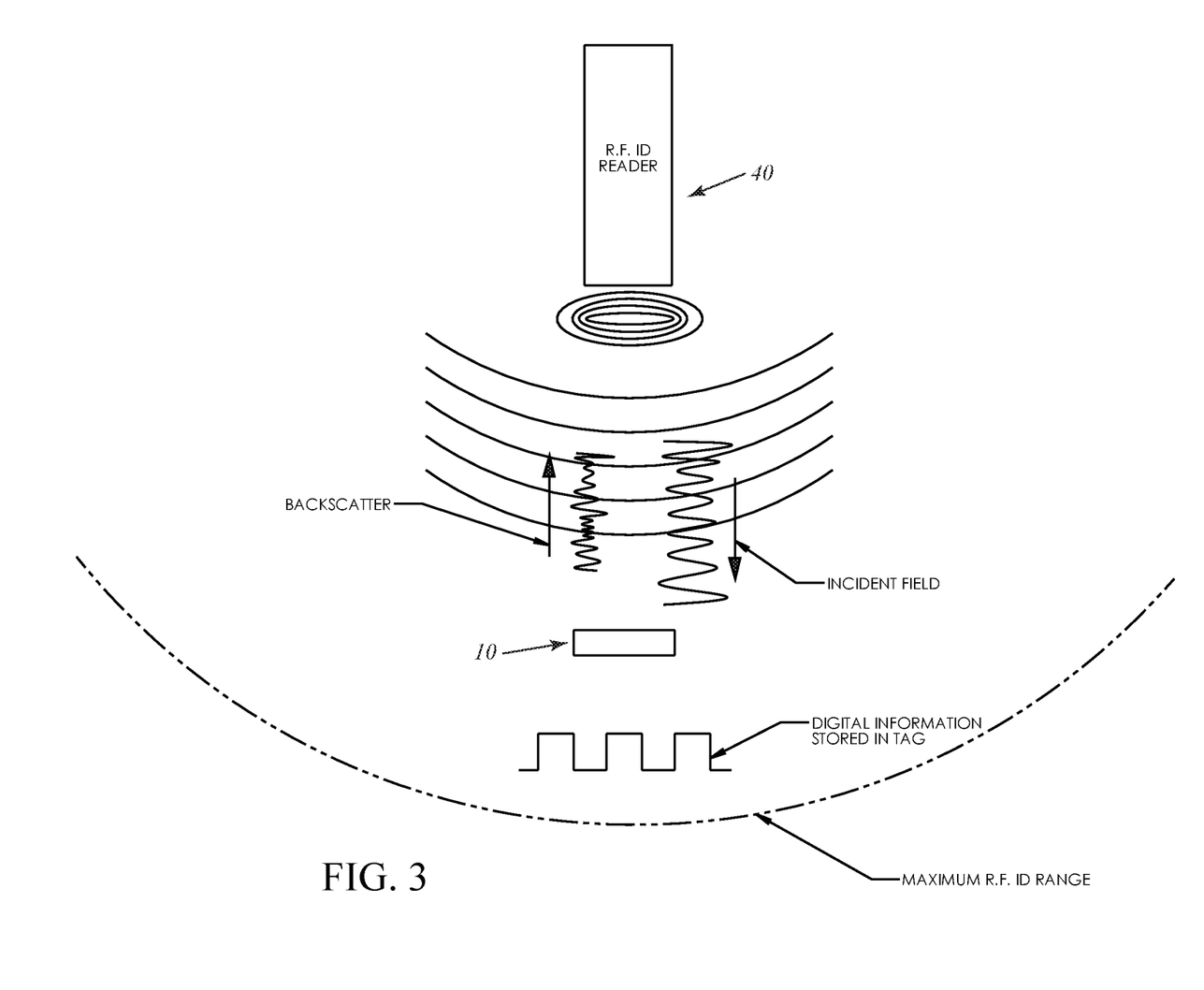
FIG. 3 is a schematic of the system of FIG. 2, showing the maximum range limit due to the tag being powered by RF energy alone.

An RFID tag generally communicates to an interrogator or reader via backscatter modulation. For example, FIG. 1 shows an example of a conventional RFID tag 10 that includes an antenna 12, a power harvesting circuit 14, a transistor switch 16, and a matching network 18. FIGS. 2 and 3 show an exemplary system including an RFID tag 10 implantable within a patient's body and a reader or transmitter 40 including an antenna 42 that transmits RF energy and establishes communication with the tag 10.

When the tag 10 desires to send a logic '0', the tag 10 connects the power harvesting circuit 14 to the antenna 12, which, with the help of the matching network 18, matches the transmitting antenna 42 in impedance achieving maximum power transfer, which can be detected by the transmitter 40 as a drop in transmit voltage level. When the tag 10 desires to send a logic '1', the tag 10 shorts across the antenna 12 with the transistor switch 16, purposely mismatching the antenna 12 so that the tag 10 emits back all energy from the transmitting antenna 42, e.g., as shown in FIG. 2.

In the special case of when the distance to the RFID tag 10 would like to be known with some precision, the maximum distance is limited because the tag 10 needs to receive enough RF energy first to power the tag 10 before the tag 10 can receive the interrogation packet from the transmitter 40 and respond. In order to rectify the RF energy, the tag 10 needs, at a minimum, to overcome the forward voltage drop of the rectification device, typically using a diode 19, such as a Schottky diode, for its low forward voltage drop, e.g., as shown in FIG. 2.

There can be other undesirable effects such as the depth of modulation since the amount of loading on the transmitter 40 is at least partially dependent on the energy harvested by the tag 10. To achieve maximum modulation requires the tag 10 always to load the antenna 12 at the maximum amount regardless of the amount of power the logic of the tag 10 needs to operate. 'Steering' the power to the tag's logic when power is needed adds complexity and would typically just not be done and therefore the level that translates to a logic '0' can vary depending on the charge level of the power harvesting circuitry. Thus, as shown in FIG. 3, the maximum range of such RFID tags may be limited based on these power needs.

Figures 4, 4A:
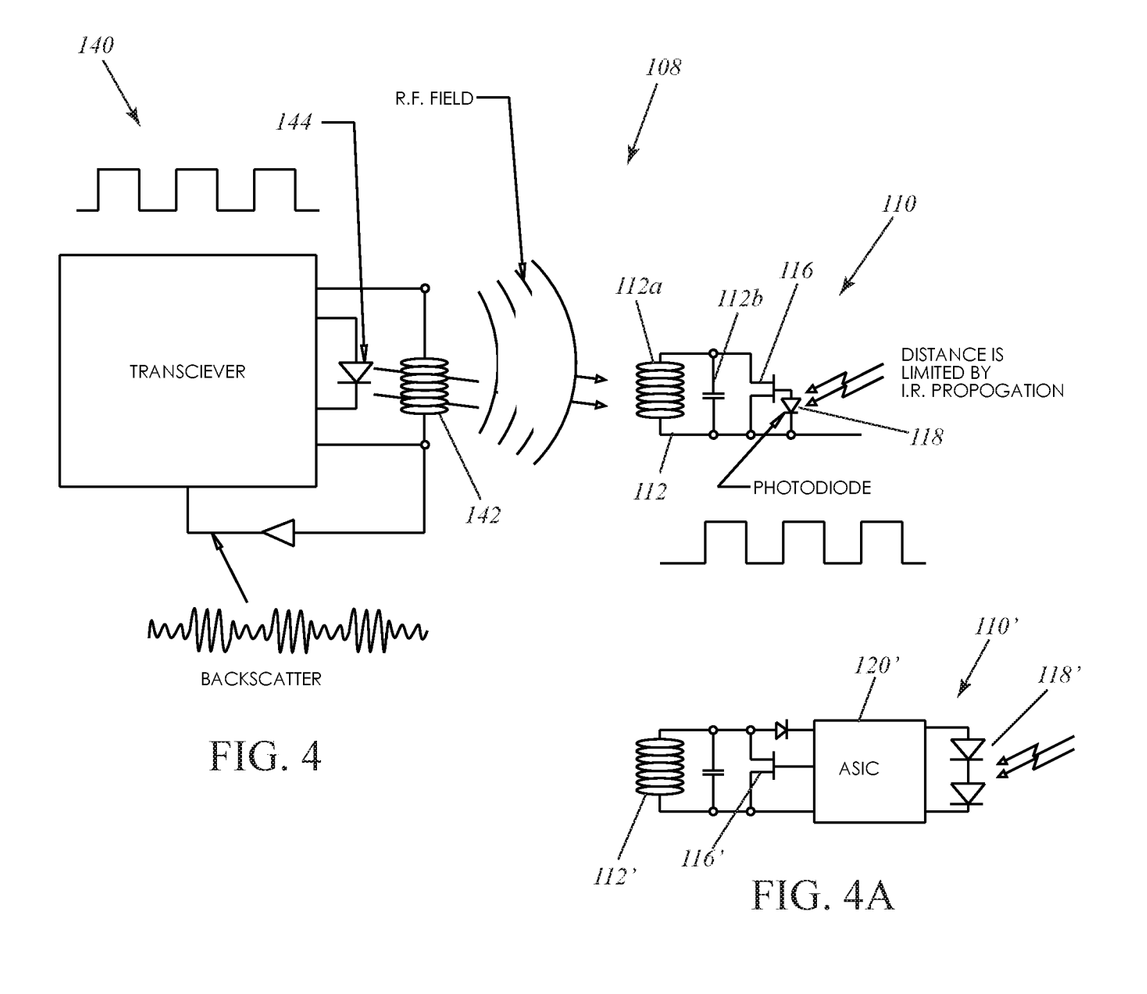
FIG. 4 is a schematic showing an exemplary embodiment of a system including an implantable tag including circuitry, powered and/or modulated by RF energy and light energy, and a reader showing representative signal processing by the reader to acquire data from the backscatter signal from the tag.
FIG. 4A is a schematic of an alternative embodiment of a tag that may be included in the system of FIG. 4 including a "smart" integrated circuit, e.g., an ASIC.
Figure 5:
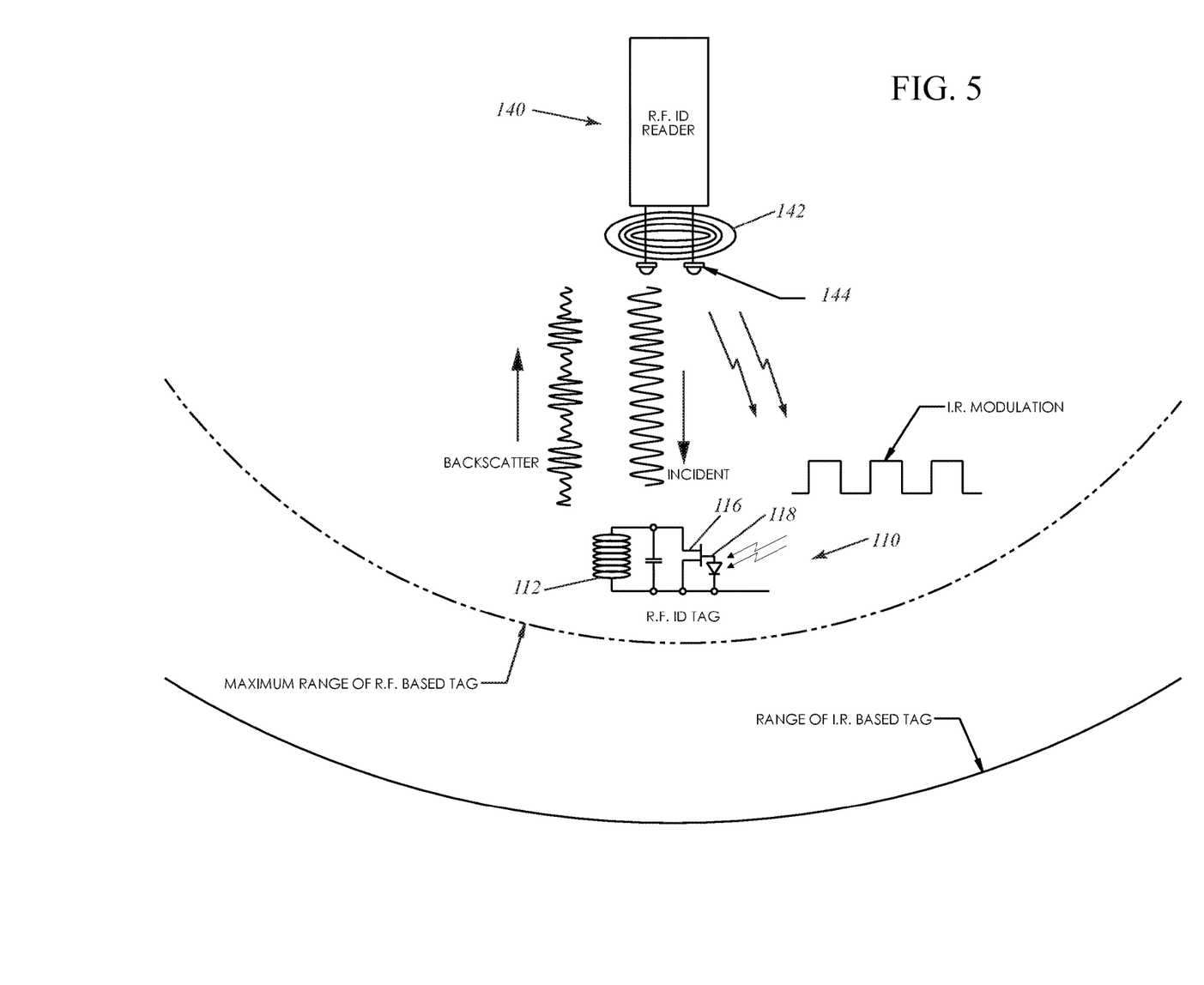
FIG. 5 is a schematic showing operation of the system of FIG. 4 with the RFID tag implanted within a patient's body and a probe or reader transmitting synchronized radiofrequency signals and infrared signals and detecting signals transmitted by the tag, which shows the increase in range that may be achieved using infrared signals to modulate the tag rather than modulating the tag based on RF energy and its internal logic/programming, as shown in FIG. 3.
Figure 6:
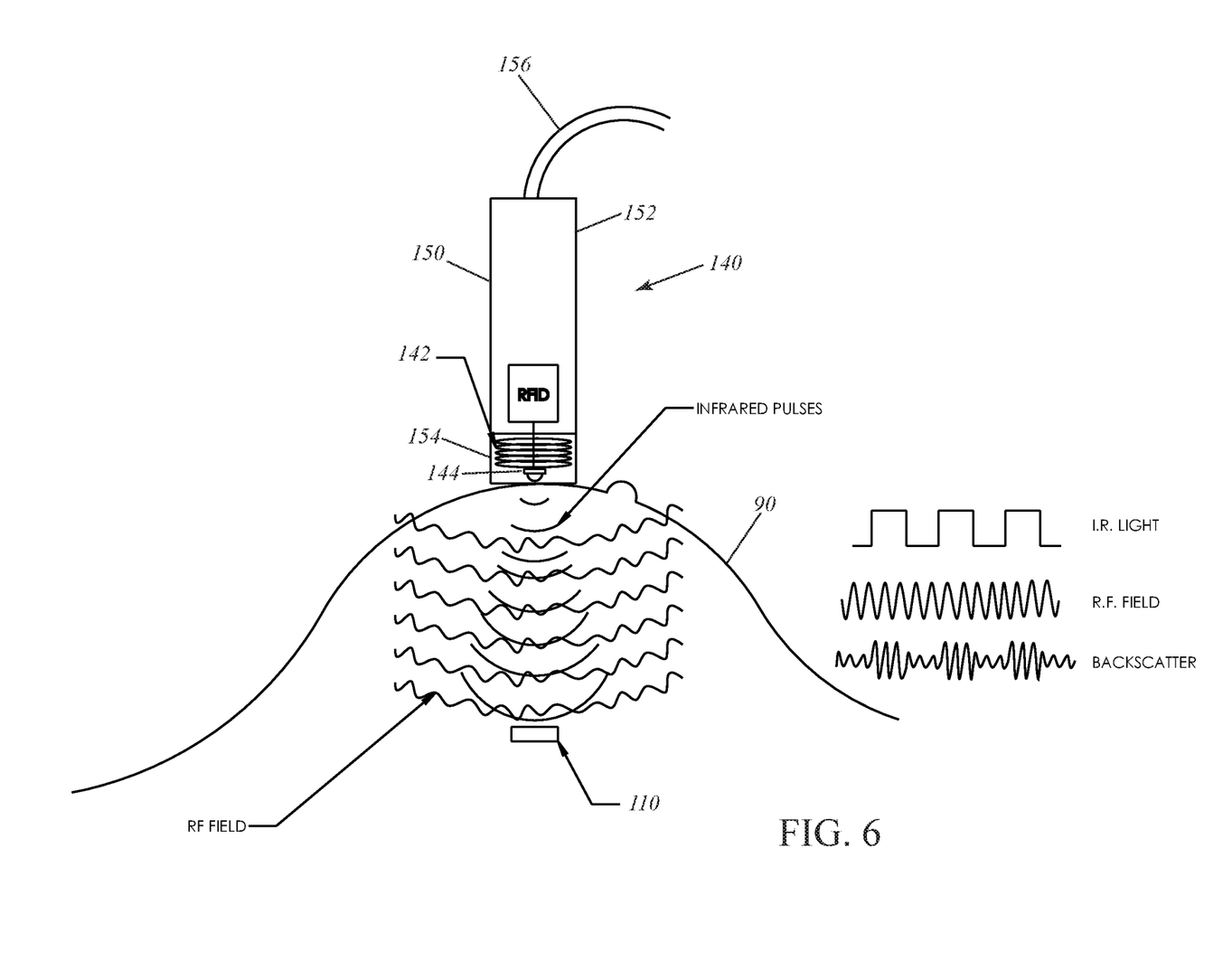
FIG. 6 is a cross-sectional view of a patient's body showing a tag implanted within a breast, and a reader placed against the patient's skin to detect, locate, and/or identify the tag. Exemplary signals are shown of the radiofrequency signals and infrared signals transmitted by the reader and the backscatter signal transmitted, in response, by the tag.

Turning to FIG. 4-6, an exemplary embodiment of a RFID tag or marker 110 is shown that uses light energy, rather than RF energy, to power the tag 110, and uses RF energy solely for detecting backscatter level and modulation for determining range. Such a configuration may optimize the tag 110 for maximum range and consistency. The loading switching may be controlled via an optical link either directly or the optical energy may be harvested to power the tag's logic to transmit back information. The tag 110 may be included in a system 108 for performing a procedure, such as a lumpectomy procedure, e.g., including a transmitter or probe 140 for transmitting synchronized radiofrequency and optical signals to the tag 110 and receiving signals from the tag 110, and a delivery device (not shown) for delivering one or more of the tags into tissue, as described further below.

Generally, the tag 110 includes an antenna 112, e.g., including a coil 112a and capacitor 112b connected in parallel, a switch, e.g., a MOSFET transistor 116 and one or more photodiodes 118 connected to the transistor 116 to provide an optically controlled RF switch. For example, as shown in FIG. 4, the photodiode 118 is connected to the gate of the transistor 118 and the source and drain are connected to the opposite ends of the antenna 112. Alternatively, as shown in FIG. 4A, the tag 110' may also include a "smart" integrated circuit, e.g., an ASIC 120', or other circuit that may be coupled to the transistor 116 and photodiode(s) 118 to harvest power and/or communicate with, e.g., receive data from and/or communicate data to, the reader 140, as described elsewhere herein.

The components of the tag 110 may be encased or embedded in an electronics package or housing (not shown) sized and configured for implantation within a patient's body. For example, a semiconductor chip, print circuit board (PCB), and/or other base may be carried in the package that includes the photodiode(s) 118, the transistor 114, and, optionally, the processor 120.' The antenna 112 may also be contained within the package, e.g., on the base, or may be located at least partially outside the package.

In an exemplary embodiment, a plurality of photodiodes 118' (e.g., as shown in FIG. 4A) may be connected in series, capable of transforming incident light striking them into electrical energy. Optionally, the photodiodes 118' may be provided in multiple pairs connected in series, which may be arranged orthogonally to one another spatially within the package (not shown). The package may be at least partially transparent or the photodiodes 118, 118' may be exposed from the package such that light directed towards the package may be received by the photodiodes 118, 118.'

In an exemplary embodiment, the photodiode(s) 118 may be configured to convert infrared light to electrical energy. One advantage of infrared energy is that it may pass sufficiently through tissue such that the reader 140, when placed against a patient's skin, may deliver sufficient energy to activate a relatively small tag 110, e.g., when implanted several inches away within the patient's body, e.g., within a breast 90, as shown in FIG. 6. Optionally, the photodiode(s) 118 (and/or a transparent surface of the package overlying the photodiode(s) 118) may include one or more coatings and/or filters, e.g., to narrow the band of infrared light striking the photodiode(s) 118, to distinguish different tags, and the like. Additional information regarding components that may be included in the tag 110 may be found in the applications incorporated by reference elsewhere herein.

With particular reference to FIG. 6, the reader 140 may be a handheld device that includes a housing 150 including a first or proximal end 152 configured to be held by a user, and a second or distal end 154 intended to be placed against or adjacent tissue, e.g., including a substantially flat or other contact surface. Generally, the reader 140 includes a transceiver module, e.g., including an exciter coil or other antenna 142, and a controller (not shown), e.g., including a signal processing module, one or more processors, one or more output devices, and the like (not shown), which may be located within the housing 150 and/or in an external control unit (also not shown), e.g., connected to the housing 150 by a cable 156.

In addition, unlike conventional RFID readers, the reader 140 includes a light transmitter 144, e.g., including one or more LEDs, light fibers, and the like (not shown), configured to transmit light, e.g., infrared light, into tissue contacted by the distal end 154, e.g., into breast tissue 90, as shown in FIG. 6. For example, light fibers terminating at the distal end 154 may extend through the cable 156 to the control unit, such that light from one or more LEDs passes through the light fibers distally to the distal end 44 of the reader 140. Optionally, the light fibers may include one or more lenses, filters, and the like (not shown), if desired, for example, to focus the light transmitted by the reader 140 in a desired manner, e.g., in a relatively narrow beam extending substantially parallel to a central axis of the reader 140, in a wider beam, and the like. Alternatively, the light source, e.g., one or more LEDs, may be located within the housing 150, e.g., adjacent the distal end 154, and one or more lenses, filters, or other components (not shown) may be coupled to the light source to direct light from the distal end 154. In an exemplary embodiment, the light source is an infrared light source, e.g., capable of delivering near infrared light between, for example, eight hundred and nine hundred fifty nanometers (800-950 nm) wavelength.

During operation, the reader 140 may simultaneously transmit radiofrequency signals and optical signals, which may be received by the tag 110. In response, the optical signals energy may modulate backscatter signals transmitted by the tag 110 and/or may be used to power the tag 110. The processor of the reader 140 may process the modulated backscatter signals received by the antenna 142 to determine information regarding the tag 110, e.g., using the amplitude and/or modulation of the backscatter signals to determine the distance from the distal end 154 to the tag 110 (i.e., the "range"). Optionally, if the tag 110 includes a smart circuit, the tag 110 may further modulate the backscatter signals to include additional information, which may be extracted from the backscatter signals, as described elsewhere herein.

For example, as shown in FIG. 5, the transmitter coil 142 of the reader 140 may transmit a uniform sine wave, e.g., at a frequency between about one hundred twenty kilohertz and two thousand four hundred fifty Megahertz (120 kHz-2450 MHz) depending on the RFID band being used, e.g., LF (125-134.2 kHz), HF (13.56 MHz), UHF (860-960 MHz), or SHF (2450 MHz). Alternatively, instead of narrow band radar signals, the reader 140 may be a probe capable of transmitting micro-impulse radar signals, e.g., at ultra-wide band frequencies ("UWB"), e.g., between about three and ten Gigahertz (3-10 GHz), as described in the applications incorporated by reference herein. Simultaneously, the light transmitter 144 may transmit infrared pulses, e.g., at a frequency between about two hundred Hertz and fifty kilohertz (200 Hz-50 kHz) or between about two hundred Hertz and ten kilohertz (200 Hz-10 kHz), both of which may be received by the tag 110. With the photodiode(s) 118 connected to the gate of the transistor 116, the transistor 116 may alternately, e.g., periodically, short the antenna 112, which may modulate the backscatter signals transmitted by the tag 110, as shown by the representative backscatter signals shown in FIG. 5. Optionally, in this embodiment, since the load switch is controlled directly from the optical link (i.e., the tag transmits no information), synchronous demodulation techniques may be utilized to further improve receiver sensitivity at the reader antenna 142 since the tag 110 is being controlled directly by the reader 140.

Alternatively, as shown in FIG. 4A, the tag 110' may include a circuit 120' coupled to the photodiodes 118' such that the infrared pulses may generate electrical energy, which may be harvested by the circuit 120.' In this alternative, the circuit 120' may store sufficient energy to activate the switch (i.e., selectively shorting the transistor 116') to include information in the backscatter signals transmitted by the antenna 112.' For example, in this embodiment, by alternating between two modes such as 'information' mode and 'distance' mode, synchronous detection may be used to identify, locate, and/or communicate with the tag 110.' In an exemplary embodiment, the circuit 120' may include a word, number, or other identifier that may be transmitted in the backscatter signals, e.g., after identifying a prompt or other interrogation signal in the incident waves from the reader 140, to distinguish the tag from other tags that may also be implanted within a patient's body. In addition or alternatively, the circuit 120' may be able to include other data or information, e.g., preprogrammed into the tag, in the signals transmitted back to the reader 140.

Thus, using a tag that receives optical signals may provide at least three benefits over a conventional RF-only powered approach.

First, the depth of modulation may be consistent because the load on the antenna 112 will always be the same and exactly the right amount for maximum coupling/loading.

Second, the maximum detectable range of tag 110 may also increase because there is no longer a minimum amount of RF energy needed to power the tag. For example, as shown in FIGS. 3 and 5, a tag using only RF energy may be limited because of the minimum level of RF energy needed, which may be weakened as the distance increases. With optical energy, the RF backscatter would be modulated no matter what the level of the RF energy, and the range would entirely be dependent on the sensitivity of the receiver. Further, if light is being used to power the tag, there is no limit on the amount of light power that may be used (as opposed to FCC and/or other regulatory limits on RF radiated power that may be transmitted into the body). Thus, the reader may be able to transmit as much optical energy as needed, e.g., to fully operate a smart circuit in the tag.

Third, if the load switch is controlled directly from the optical link (i.e., the tag transmits no information), then this opens up the possibility for synchronous demodulation techniques to be utilized to further improve receiver sensitivity since the tag is being controlled directly by the transmitter. Also, by alternating between two modes such as 'information' mode and 'distance' mode, synchronous detection could also be exploited for the case of an intelligent tag as well.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for identifying or locating a target region within a patient's body, comprising:
    a probe comprising one or more probe antennas for transmitting radiofrequency signals into a patient's body and receiving backscatter signals transmitted from the patient's body, and a light source for delivering optical signals into a patient's body; and
    a tag sized for implantation within a patient's body, the tag comprising a tag antenna, an energy converter configured to transform the optical signals from the light source into electrical energy, and a switch coupled to the energy converter such that the optical signals cause the tag to modulate backscatter signals transmitted by the tag antenna in response to the transmitted radiofrequency signals and received by the probe.

2. The system of claim 1, wherein the switch is coupled to the tag antenna and the energy converter such that, when light from the optical signals is received by the energy converter, the tag antenna is shorted and transmits substantially all radiofrequency energy received by the tag antenna back to the probe in the backscatter signals.

3. The system of claim 1, wherein the light source comprises an infrared light source configured to emit infrared light pulses, and wherein the energy converter comprises one or more photodiodes configured to convert the infrared light pulses into electrical energy.

4. The system of claim 3, wherein the switch is coupled to the one or more photodiodes such that the infrared light pulses cause the one or more photodiodes to alternately short the tag antenna to modulate the backscatter signals transmitted by the tag antenna.

5. The system of claim 3, wherein the switch comprises a field effect transistor (FET), the one or more photodiodes coupled to a gate of the FET.

6. The system of claim 1, wherein the tag antenna comprises a coil.

7. The system of claim 1, wherein the tag further comprises a harvesting circuit for harvesting electrical energy from the energy converter to power a control circuit of the tag to modulate the backscatter signals transmitted by the tag antenna.

8. The system of claim 7, wherein the control circuit is configured to modulate the backscatter signals to include data related to the tag, and wherein the probe comprises a signal processor for extracting the data from the backscatter signals received from the tag.

9. The system of claim 7, wherein the control circuit is configured to alternate the tag between an information mode and a distance mode.

10. The system of claim 8, wherein the data comprises an identifier to distinguish the tag from other tags.

11. A system for identifying or locating a target region within a patient's body, comprising:
    a probe comprising one or more probe antennas for transmitting electromagnetic signals into a patient's body and receiving signals from the patient's body, and a light source for delivering optical signals into a patient's body; and
    a tag sized for implantation within a patient's body, the tag comprising a tag antenna, an energy converter configured to transform the optical signals from the light source into electrical energy, and a switch coupled to the energy converter such that the optical signals cause the tag to modulate electromagnetic signals transmitted by the tag antenna and received by the probe.

12. The system of claim 11, wherein the probe comprises a transmitter configured to transmit radiofrequency signals and receive backscatter signals transmitted by the tag in response to the transmitted radiofrequency signals, the energy converter configured to modulate the backscatter signals based at least in part on the optical signals.

13. The system of claim 12, wherein the switch is coupled to the tag antenna and the energy converter such that, when light from the optical signals is received by the energy converter, the tag antenna is shorted and transmits substantially all radiofrequency energy received by the tag antenna back to the probe.

14. The system of claim 11, wherein the light source comprises an infrared light source configured to emit infrared light pulses, and wherein the energy converter comprises one or more photodiodes configured to convert the infrared light pulses into electrical energy.

15. The system of claim 14, wherein the switch is coupled to the one or more photodiodes such that the infrared light pulses cause the one or more photodiodes to alternately short the tag antenna to modulate the electromagnetic signals transmitted by the tag antenna.

16. The system of claim 15, wherein the switch comprises a field effect transistor (FET), the one or more photodiodes coupled to a gate of the FET.

17. The system of claim 11, wherein the tag antenna comprises a coil.

18. The system of claim 11, wherein the tag further comprises a harvesting circuit for harvesting electrical energy from the energy converter to power a control circuit of the tag to modulate the electromagnetic signals transmitted by the tag antenna.

19. The system of claim 18, wherein the control circuit is configured to modulate the electromagnetic signals to include data related to the tag, and wherein the probe comprises a signal processor for extracting the data from the electromagnetic signals received from the tag.

20. The system of claim 18, wherein the control circuit is configured to alternate the tag between an information mode and a distance mode.

* * * * *